(12) United States Patent
Jennewein et al.

(10) Patent No.: US 6,727,243 B1
(45) Date of Patent: Apr. 27, 2004

(54) COMPOSITIONS COMPRISING CEFUROXIME AXETIL

(75) Inventors: Herwig Jennewein, Absam (AT); Johannes Raneburger, Wörgl (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/445,741

(22) PCT Filed: Nov. 24, 1999

(86) PCT No.: PCT/EP99/09096

§ 371 (c)(1),
(2), (4) Date: Dec. 10, 1999

(87) PCT Pub. No.: WO00/30647

PCT Pub. Date: Jun. 2, 2000

(30) Foreign Application Priority Data

Nov. 26, 1998 (AT) .................................. 1989/98

(51) Int. Cl.⁷ ...................... A61K 31/54; A61K 31/545; A61K 47/32
(52) U.S. Cl. .................. 514/224.2; 514/202; 514/772.4
(58) Field of Search .............................. 514/772.4, 202, 514/224.2

(56) References Cited

U.S. PATENT DOCUMENTS 6,107,290 A    8/2000  Woo et al. .................. 514/200

FOREIGN PATENT DOCUMENTS

| DE | 198 35 823 A1 | | 10/1999 |
|---|---|---|---|
| EP | 107 276 A2 | | 5/1984 |
| EP | 280 571 A2 | | 8/1988 |
| GB | 1 571 683 | | 7/1980 |
| GB | 1 572 993 | | 8/1980 |
| GB | 2127401 | * | 4/1984 |
| GB | 2 127 401 A | | 4/1984 |
| GB | 2 181 052 A | | 9/1986 |
| GB | 2 204 792 A | | 11/1988 |
| GB | 2204792 | * | 11/1988 |
| WO | WO 98/22091 | | 5/1998 |
| WO | 99 08683 | | 2/1999 |
| WO | 99 44614 | | 9/1999 |
| WO | 99 62559 | | 12/1999 |
| WO | 01 10410 A1 | | 2/2001 |

OTHER PUBLICATIONS

United States Food and Drug Administration: "Antibiotic drugs; Cefuroxime axetil tablets" Federal Register, vol. 52, No. 214, pp. 42431–42434, XP000901055 (1987).

* cited by examiner

*Primary Examiner*—Alton Pryor
(74) *Attorney, Agent, or Firm*—Peter J. Waibel

(57) ABSTRACT

Cefuroxime axetil in a non-gelatinous form on contact with an aqueous liquid, e.g., in the form of a solid dispersion on a carrier, e.g., useful for the production of pharmaceutical compositions comprising cefuroxime axetil as an active ingredient and use of cefuroxime axetil in the manufacture of an oral dosage form which does not exhibit an adverse food effect.

28 Claims, 3 Drawing Sheets

Zinnat

Film-Coated Tablet – Present Invention

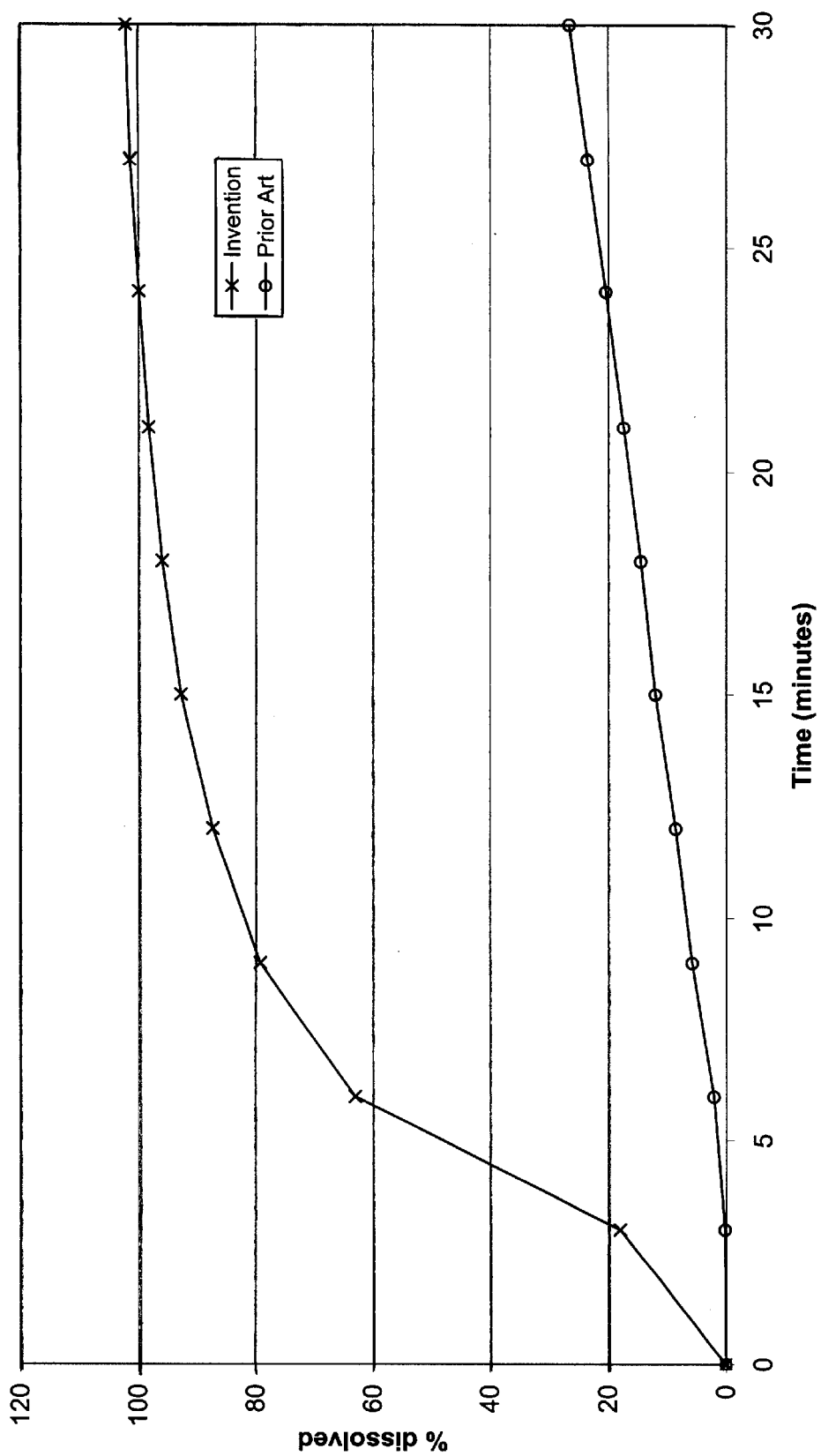

COMPOSITIONS COMPRISING CEFUROXIME AXETIL

Figure 1:
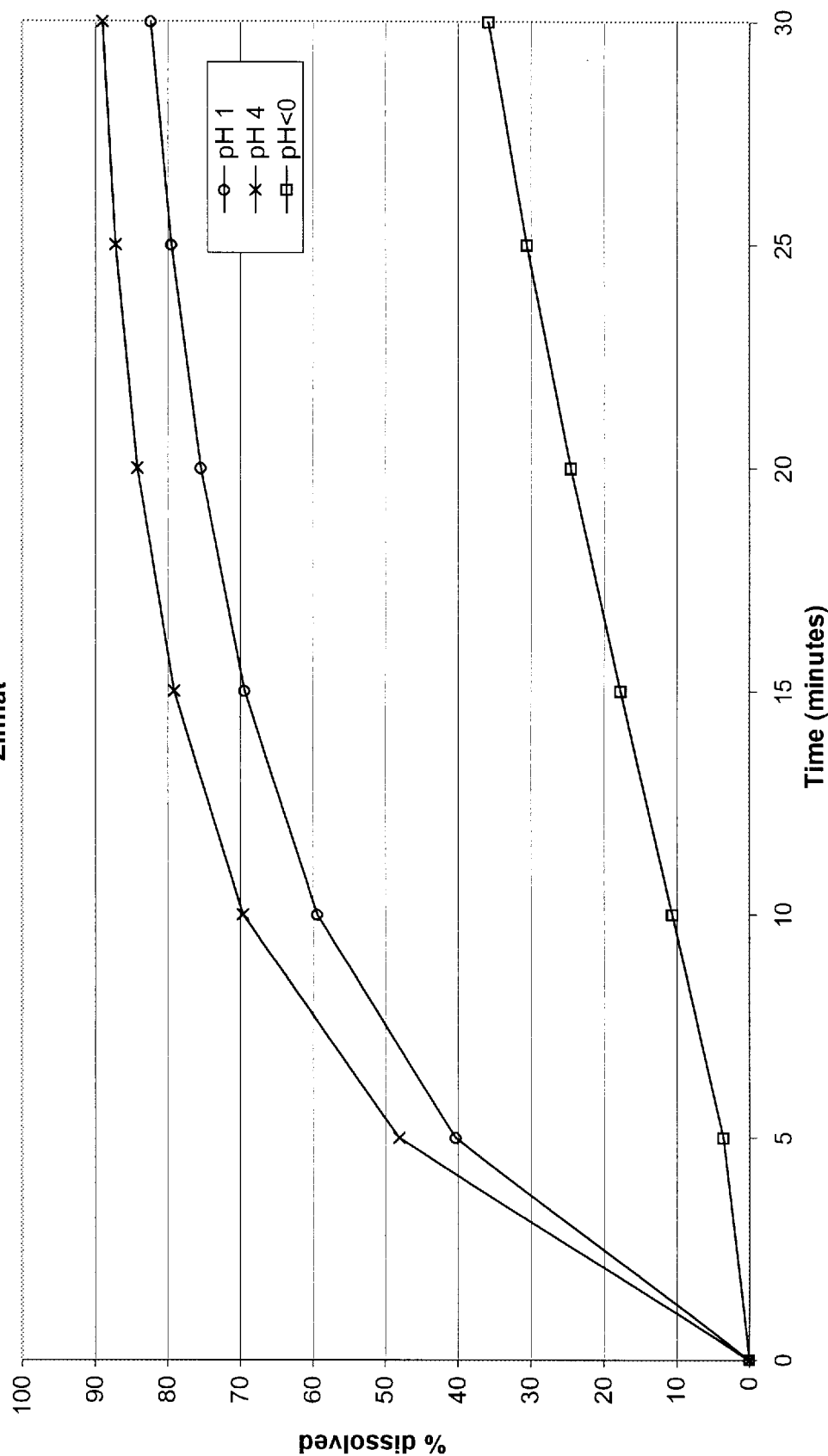

This Application is a 371 of PCT/EP99/09096 filed Nov. 24, 1999.

The present invention relates to β-lactam compositions, specifically in respect with cefuroxime axetil which is the 1-acetoxyethyl ester of cefuroxime and which is a well known second generation cephalosporin antibiotic, e.g. useful in the treatment of microbial infections, e.g. described in The Merck Index, 12th edition, p. 324 and 325, no. 2002. The in vivo active ingredient in cefuroxime axetil is cefuroxime because in vivo the carboxylic ester in position 4 of the ring system is split off, the carboxylic acid is set free and the compound cefuroxime is formed.

Cefuroxime axetil, e.g. in crystalline form or in amorphous form, may for example be administered orally, e.g. in the form of, e.g. film-coated, tablets, or in the form of a dry powder which may e.g. be administered as such, e.g. together with an aqueous liquid or, reconstituted with an aqueous liquid, e.g. water, in the form of a suspension/syrup. However cefuroxime axetil in crystalline or in amorphous form may undergo gelatination, e.g. it may form a gelatinous mass, in contact with an aqueous liquid, e.g. water or salvia; e.g. a gel may be formed on the surface of, e.g. galenically formulated, cefuroxime axetil particles. Gelatination, e.g. gel formation on the surface of, e.g. galenically formulated, cefuroxime axetil particles, may result in poor dissolution of cefuroxime axetil, with e.g. the consequence that adsorption of cefuroxime axetil from the gastrointestinal tract may be reduced.

It was now surprisingly found that gelatination of cefuroxime axetil, e.g. gel formation on the surface of, e.g. galenically formulated, cefuroxime axetil particles, upon contact with an aqueous liquid may be, e.g. substantially, avoided if cefuroxime axetil is neither in crystalline nor amorphous form, but in non-gelatinous form on contact with an aqueous liquid.

Although it is not intended to be bound on any theory it is believed that in a non-gelatinous form on contact with an aqueous liquid according to the present invention cefuroxime axetil may be incorporated in a polymer in the form of a molecular dispersion which is a solid solution of cefuroxime axetil in the polymer; and/or in the form of a surface solid (molecular) dispersion on an adsorbent.

A non-gelatinous form, e.g. galenically formulated, of cefuroxime axetil, e.g. which does not form a gel on the surface of cefuroxime particles, on contact with an aqueous liquid according to the present invention and as used herein includes a form of cefuroxime axetil, e.g. galenically formulated cefuroxime axetil, e.g. a dosage form, e.g. solid, e.g. containing cefuroxime axetil as active ingredient and pharmaceutically acceptable excipients, having a dissolution rate of the active ingredient at 37° C. in aqueous medium, e.g. acidic, e.g. hydrochloric acid-acidic, e.g. buffered, which is higher, equal, or not lower than 5% at a pH of around 1, e.g. at pH 1 after 10 to 15 minutes from the start of the dissolution test; and/or than 20% at a pH<0 after 25 to 30 minutes from the start of the dissolution test, than the dissolution rate of the active ingredient at a pH of around 4, e.g. at pH 4.

Cefuroxime axetil in non-gelatinous form on contact with an aqueous liquid thus includes cefuroxime axetil in a form, e.g. galenically formulated, having a dissolution rate which is substantially pH independent, e.g. at pH<0, pH 1, and pH 4.

An appropriate method to determine said dissolution rate includes e.g. a method as conventional, e.g. determining the dissolution rate of cefuroxime axetil, e.g. in a dosage form, as set forth in USP(US Pharmacopaea) test <711> in a USP-2 apparatus under conditions at least as stringent as the following: 900 ml of an aqueous medium, 37° C. with paddles turning at 55 rpm; determining an average dissolution rate of at least 6 samples, containing substantially the same amount of cefuroxime axetil, and substantially the same excipients in substantially the same amount; at appropriate pH, e.g. at (around) pH 4, at (around) pH 1 and pH<0. Dosage forms which pass this test under more stringent conditions, e.g. lower volume of aqueous medium, lower temperature, lower paddle speed, are also included under the above definition. An appropriate aqueous medium useful for determination at pH 4 comprises e.g. an acetate buffer (pH 4) e.g. according to USP; and for determination at (around) pH 1 and pH<0 an hydrochloric acid-acidic aqueous solution having the appropriate pH. Detection of the dissolution rate of cefuroxime axetil at a defined time point may be carried out according to a method as conventional, e.g. by means of UV, HPLC.

In one aspect the present invention provides cefuroxime axetil in a non-gelatinous form on contact with an aqueous liquid, e.g. water, e.g. in the form of a solid solution in a polymer; e.g. in a weight ratio of cefuroxime axetil:polymer of 1:0.1 to 1:0:8, e.g. 1:0.15 to 1:08, such as 1:0.15 to 1:06, e.g. 1:0.35 to 1:0.6, e.g. 1:0.35 to 1:0.55, e.g. 1:0.35 to 1.0.45; or in the form of a surface solid dispersion on an adsorbent, e.g. in a weight ratio cefuroxime axetil:adsorbent of 1:0.1 to 1:1.5; e.g. 1:03 to 1.1.3, preferably in the form of a solid solution in a polymer.

Cefuroxime axetil in non-gelatinous form, e.g. in the form of a solid solution in a polymer or in surface solid dispersion may be e.g. obtained as follows: A solution or suspension of cefuroxime axetil in free form, e.g. in crystalline form, or in amorphous form, e.g. in the form of a solvate or in non-solvate form, and of a polymer and/or of adsorbent may be produced in organic solvent, e.g. in the presence of water.

A polymer includes polymer, e.g. one or more, which is able to form a solid solution of cefuroxime axetil in a polymer, e.g. according to the definition of cefuroxime axetil in non-gelatinous form on contact with an aqueous liquid as indicated above, preferably polymer which is soluble in the solvent (system) used. A polymer includes preferably a pharmaceutically acceptable polymer, e.g. a homo- and a copolymer, e.g. a homo- and a copolymer of a polyvinylpyrrolidone, e.g as commercially available under the trade name Kollidon®, e.g a homopolymer such as a povidone, cross-linked povidone, e.g. crospovidone, polyplasdone; and a polyvinylpyrrolidone copolymer; polyethylene glycol, polyethylene oxide, cellulose. Cellulose include alkylcelluloses, e.g. methyl-, ethyl-, propylcelluloses; hydroxalkylcelluloses, e.g. hydroxymethylcellulose, hydroxyethylcellulose, hydroxyproylcellulose; hydroxypropylmethylcellulose, and a cellulose which is, e.g. chemically, modified, e.g. which carry carboxyl groups as substituents, such as a carboxymethylcellulose. Preferred is a polyvinylpyrrolidone, e.g. as commercially available under the trade name Kollidon®, e.g. povidone, cross-linked povidone, e.g. crospovidone or polyplasdone, polyvinylpyrrolidone copolymer, celluloses, e.g. alkylcelluloses, hydroxylkylcelluloses, hydroxymethylpropylcelluloses; for example ethyl- and propylcelluloses, hydroxymethylcellulose, hydroxyethylcellulose, hydroxypropylmethylcellulose, a cellulose which is, e.g. chemically, modified, e.g. which carry carboxyl groups as substituents, polyethylene oxide, crospovidone and polypalsdone, and a copolymer of polyvinylpyrrolidone.

Preferred is a polyvinylpyrrolidone copolymer, such as vinylpyrrolidone-vinylacetate copolymer, e.g. consisting of N-vinyl-2-pyrrolidone and vinyl acetate, e.g. in a random 60:40 ratio, e.g. having units of formula

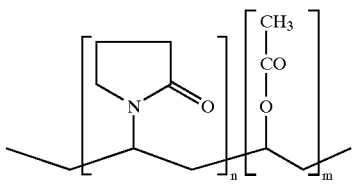

e.g. as commercially available under the trade name Kollidon® (e.g. VA64) or Plasdone® (e.g. S-630). An appropriate weight ratio of cefuroxime axetil and the polymer include a ratio of 1:0.1 to 1:0:8, e.g. 1:0.15 to 1:08, such as 1:0.15 to 1:06, e.g. 1:0.35 to 1:0.6, e.g. 1:0.35 to 1:0.55, e.g. 1:0.35 to 1.0.45.

Appropriate adsorbent includes, e.g. pharmaceutically acceptable, adsorbent, e.g. one or more, which is able to form a surface solid dispersion with cefuroxime axetil, e.g. according to the definition of cefuroxime axetil in non-gelatinous form on contact with an aqueous liquid as indicated above, e.g. material which is able to bind other material on its surface and to form a solid (molecular) dispersion, such as silicium dioxide, e.g. colloidal, such as for example Aerosil®, e.g. Aerosil® 200, preferably colloidal silicium dioxide. Preferably the adsorbent itself is biologically inactive. An appropriate weight ratio of cefuroxime axetil:adsorbent includes e.g. 1:0.1 to 1:1.5, e.g. 1:0.3 to 1:1.3.

A non-gelatinous form of cefuroxime axetil may comprise both, polymer and adsorbent. A preferred weight ratio of cefuroxime axetil:polymer plus adsorbent includes e.g. a weight ratio of 1:0.3 to 1:1.8, e.g. 1:0.3 to 1:0.9.

In another aspect the present invention provides cefuroxime axetil in non-gelatinous form on contact with an aqueous liquid which comprises cefuroxime axetil in the form of a solid solution in a polymer in combination with cefuroxime axetil in the form of a solid dispersion on an adsorbent; e.g. in a weight ratio of cefuroxime axetil:adsorbent of 1:0.1 to 1:1.5, e.g. 1:0.3 to 1:1.3.

Appropriate organic solvent include one or more organic solvents, e.g. a solvent system, wherein cefuroxime axetil and the polymer are soluble, and wherein the adsorbent is preferably insoluble, or only soluble to a slight extent, e.g. colloidal soluble. E.g. water may be present in organic solvent, e.g. if the adsorbent, if present, is insoluble or only slightly soluble, e.g. colloidal, in water. Preferred organic solvent includes one single organic solvent or a mixture of organic solvent, e.g. in the presence of water, e.g. a ketone, e.g. acetone, an alcohol, e.g. ethanol; and an halogenated hydrocarbon, e.g. methylene chloride. Preferred organic solvent includes ketones, e.g. in the presence of water, e.g. up to (around) 30% v/v of the organic solvent.

A solution or suspension of cefuroxime axetil and the polymer and/or adsorbent in organic solvent, e.g. in the presence of water, may be obtained, e.g. upon (slight) heating of the mixture.

A non-gelatinous form of cefuroxime axetil on contact with an aqueous liquid may be e.g. obtained by removal of the solvent from the solution or suspension comprising cefuroxime axetil and the polymer and/or adsorbent in organic solvent, e.g. in the presence of water, by solvent removal, e.g. solvent evaporation, such as rotovapor evaporation, spray drying, spray granulation, such as fluidized bed granulation; preferably spray drying or spray granulation. A non-gelatinous form of cefuroxime axetil on contact with an aqueous liquid is e.g. useful in the production of a granulate, which granulate is e.g. useful for producing pharmaceutical formulations, e.g. tablets, or a powder, e.g. dry powder, e.g. useful for oral administration comprising cefuroxime axetil as an active ingredient.

In another aspect the present invention provides a process for the production of cefuroxime axetil in non-gelatinous form on contact with an aqueous liquid comprising dissolving or suspending cefuroxime axetil and a polymer, e.g. in a weight ratio of cefuroxime axetil:polymer of 1:0.1 to 1:0:8; or an adsorbent, e.g. in a weight ratio cefuroxime axetil:adsorbent of 1:0.1 to 1:1.5; or a polymer plus an adsorbent in a weight ratio of cefuroxime axetil: polymer plus an adsorbent of 1:0.3 to 1:1.3; in organic solvent, e.g. in the presence of water, e.g. in ketone, e.g. acetone; or in alcohol, e.g. ethanol, e.g. in the presence of a ketone and/or an alcohol as the sole organic solvent; and removing the solvent.

Cefuroxime axetil in non-gelatinous form on contact with an aqueous liquid is e.g. useful in the production of a pharmaceutical composition. A pharmaceutical composition may e.g. be produced according to a method as conventional using ceforuxime axetil in non-gelatinous form on contact with an aqueous liquid as the active ingredient, or e.g. according to a method as as described herein.

In another aspect the present invention provides a pharmaceutical composition, e.g. dosage form, e.g. solid, e.g. oral, e.g. in the form of tablet, dragee, (dry) powder; comprising a pharmaceutically effective amount of cefuroxime axetil in non-gelatinous form on contact with an aqueous liquid as an active ingredient, e.g. wherein the active agent consists essentially of cefuroxime axetil, e.g. in an amount which correponds to an amount of cefuroxime of 50 to 1000 mg, e.g. 50 to 800 mg, such as 100 to 600 mg, e.g. 125 mg, e.g. 250 mg, e.g. 500 mg; in combination with, e.g. conventional, pharmaceutically acceptable excipients, e.g. which are suitable for the preparation of, e.g. oral, pharmaceutical compositions, e.g. compositions which are administered orally.

It was found that pharmaceutical compositions according to the present invention, e.g. dosage forms, comprising cefuroxime axetil in non-gelatinous form on contact with an aqueous liquid according to the present invention in combination with pharmaceutically acceptable excipients may meet the requirements of USP 23 (dissolution) and USP 24 (provided; and supposed to be in force from the year 2000), i.e. said dosage forms effect at least 60% (Q-value) dissolution of the labeled amount of cefuroxime axetil within 15 minutes, e.g. and, e.g. and/or, at least 75% (Q-value) dissolution of the labeled amount of cefuroxime axetil within 45 minutes; when a dosage form of cefuroxime axetil is tested as set forth in USP test <711> in a USP-2 apparatus under conditions at least as stringent as the following: 900 ml 0.07 N hydrochloric acid, 37° C. with paddles turning at 55 rpm.

In another aspect the present invention provides a pharmaceutical dosage form, e.g. solid, compising cefuroxime axetil in an pharmaceutically effective amount in non-gelatinous form on contact with an aqueous liquid as an active agent in combination with pharmaceutically acceptable excipients wherein said dosage form effects at least 60% (Q-value) dissolution of the labeled amount of cefuroxime axetil within 15 minutes, e.g. and/or at least 75% (Q-value) dissolution of the labeled amount of cefuroxime axetil within 45 minutes; when a dosage form of cefuroxime axetil is tested as set forth in USP test <711> in a USP-2 apparatus under conditions at least as stringent as the following: 900 ml 0.07 N hydrochloric acid, 37° C. with paddles turning at 55 rpm.

It has been found that cefuroxime axetil in non-gelatinous form on contact with an aqueous liquid according to the present invention may be obtained in the form of a granulate comprising beside cefuroxime axetil pharmaceutically acceptable excipients, e.g. components, which are useful in the production of a granulate.

In another aspect the present invention provides a granulate comprising cefuroxime axetil and a polymer and/or an adsorbent wherein cefuroxime axetil is in non-gelatinous form on contact with an aqueous liquid, e.g. wherein cefuroxime axetil is a solid solution in the polymer and/or is a surface solid dispersion on an adsorbent; and pharmaceutically acceptable excipient; e.g. one or more; e.g. surface active agent, e.g. carrier, e.g. lubricant; e.g. containing cefuroxime axetil in 25 to 95 weight %; polymer in 0 to 75 weight %, e.g. 5 to 75 weight %; adsorbent in 0 to 60 weight %, e.g. 5 to 50 weight %; surface active agent in 0 to 5 weight %, e.g. 0.3 to 1.5 weight %; carrier in 0 to 50 weight %, e.g. 5 to 50 weight %; and/or lubricant in 0 to 5 weight %, e.g. 0.1 to 5 weight %.

A granulate according to the present invention comprises agglomerated or aggregated particles of granulate-component-substances. A granulate according to the present invention may e.g. be in the form of powder, grains, granules.

A granulate according to the present invention may be e.g obtained according to a method as conventional, or e.g. as follows: From a solution or a suspension containing cefuroxime axetil in non-gelatinous form on contact with an aqueous liquid according to the present invention; e.g. pre-prepared as described above in the process for the production of cefuroxime axetil in non-gelatinous form; or from a solution or suspension containing cefuroxime axetil and a polymer and/or an adsorbent in organic solvent, e.g. in the presence of water; comprising one or more pharmaceutically acceptable excipients, e.g. components, the solvent may be removed. The solvent from said solution or suspension may be e.g. removed according to a method as conventional, or e.g. by mixing/stirring the solution or suspension of cefuroxime axetil, polymer and/or adsorbent and pharmaceutical excipient, e.g. under elevated temperature, e.g. in a vacuum; under solvent removal, e.g. under use of a rotovapor, spray drying, spray granulation, e.g. fluidized bed granulation, preferably spray drying, spray granulation.

In case of use of a carrier, e.g. fluidized bed granulation may conveniently be used, e.g. a solution of cefuroxime axetil containing a polymer and/or an adsorbent, e.g. and one or more pharmaceutically acceptable excipients, may be sprayed onto a pre-prepared fluid of the solid carrier, e.g. which fluid may comprise one or more further pharmaceutically acceptable excipients, e.g. in solid form e.g. lubricants. Spray drying and rotovapor evaporation may be e.g. carried out according to a method as conventional.

E.g. pharmaceutically acceptable excipient which is preferred in a granulate according to the present invention includes, e.g. one or more, surface active agent, e.g. which influences the forces of surfaces of chemical entities, e.g. which lower the surface tension of a liquid, e.g. the use of which may result in easier wetting and/or easier emulgation of a solid in a liquid, e.g. including, e.g. ionic or non-ionic, surfactant, wetting agent, tenside; such as sulphonates and sulphates of fatty acid alcohols, e.g. sodium laurylsulphate; Texapon® which includes different types of washing raw material, e.g. sulphates or ethersulphates of fatty acid alcohols, e.g.sodium- and ammoniumlauryl sulphate, e.g. a mixture of sodium and ammonium laurylsulphate, preferably sodium laurylsulphate;

carrier, e.g. inert material which may be used as a core, e.g. in a fluidized bed granulation as a core for active ingredient, e.g. such as a conventional core, e.g. sugar, including sugar alcohols, e.g. mannitol (mannite), which includes mannitol-granulates, e.g. Pearlitol®, such as Pearlitol® SD 200;

lubricant, e.g. talcum, Mg-stearates.

A granulate of cefuroxime axetil in non-gelatinous form on contact with an aqueous liquid, comprising one or more pharmaceutically acceptable excipients may be obtained upon removal of the solvent. E.g. a granulate according to the present invention may contain in weight % of the granulate weight: Cefuroxime axetil 25 to 95%, e.g. 30 to 85% Polymer 0 to 75%; if present 5 to 75%, e.g. 10 to 60%, such as 15 to 60%; preferably 15 to 60% if a granulate is obtained by spray granulation; and preferably 25 to 45% if a granulate is obtained by spray drying; Adsorbent: 0 to 60%, e.g. 0 to 50%; if present 5 to 50%; Surface active agent 0 to 5%, e.g. 0 to 2.5%, e.g. 0.3 to 1.5%; Carrier: 0 to 50%, e.g. 0 to 40%, e.g. 0 to 30%; if present e.g. 5 to 50%; Lubricant: 0 to 5%, e.g. 0 to 2.5%, e.g. 0 to 1.0%; if present e.g. 0.1 to 1.0%, e.g. 0.1 to 0.5%; but containing at least one pharmaceutically acceptable excipient.

In another aspect the present invention provides a process for the production of a granulate wherein cefuroxime axetil is in non-gelatinous form on contact with an aqueous liquid, comprising removing solvent from a suspension or solution containing cefuroxime axetil and a polymer and/or an adsorbent which are able to form a non-gelatinous form on contact with an aqueous liquid with cefuroxime axetil; or cefuroxime axetil in a non-gelatinous form on contact with an aqueous liquid; e.g. pre-prepared, e.g. as described above; and pharmaceutically acceptable excipient; e.g. one or more; in organic solvent, e.g. in the presence of water.

A granulate of cefuroxime axetil in non-gelatinous form containing one or more pharmaceutically acceptable excipients may be obtained, e.g. which is suitable in the production of pharmaceutical compositions, e.g. oral, e.g. after further processing, such as in the production of an, e.g. dry, powder for oral administration which is e.g. suitable for administration as such, or suitable in the preparation of suspension/syrup.

A dry powder according to the present invention may be obtained e.g. by a method as conventional, or, e.g. as follows: A granulate according to the present invention, e.g. after further processing, e.g. including processing through a sieve, milling; may be mixed with one or more pharmaceutically acceptable excipient, e.g. auxiliaries, e.g. which is useful in the production of a dry powder for oral administration. Mixing may be carried out e.g. according to a method as conventional. A dry powder for oral administration may be e.g. in the form of powder, grains, granules, e.g. having a desired particle size. A mixture obtained, e.g. a final powder/grain/granule mixture, or an intermediate-powder/grain/granule mixture obtained, may be further processed, e.g. granulated, compacted, broken, milled, sieved, e.g. to obtain any desired particle size, e.g. according to a method as conventional. Pharmaceutically acceptable excipient which are useful in the production of a dry powder for oral administration according to the present invention include, e.g.

sugar, e.g. chemically modified, e.g. fructose, glucose, saccharose, sugar alcohol, e.g. chemically modified, sweetener, e.g. nutritive and artificial, aspartam;

filler including modified starches, e.g. starch 1500 (pre-gelatinzed starch);

thickener, e.g. guar flour;

binder, e.g. polyvinylpyrrolidones, celluloses;

flavoring agent, preservative, surfac active agent, dye-stuff; preferably sugar and/or sweetener and/or filler and/or thickener, and/or preservative.

In another aspect the present invention provides a dry powder, e.g. in the form of powder, grains, granules, e.g. having a desired particle size, for oral adminstration, e.g. suitable for administration as such, e.g. together with an aqueous liquid, e.g. water and e.g. suitable for the preparation of suspension/syrup, comprising an effective amount of cefuroxime axetilin non-gelatinous form on contact with an aqueous liquid as an active ingredient, e.g. which may be reconstituted with an aqueous liquid, e.g. water, to obtain a suspension/syrup; e.g. in a dosage form, e.g. comprising a desired amount of cefuroxime axetil in a desired volume; and pharmaceutically acceptable excipient; e.g. which is suitable in the production of a dry powder, e.g. sugar and/or sweetener and/or filler and/or thickener, and/or preservative.

A dry powder according to the present invention may be provided in a pharmaceutical dosage form, e.g. in a container, e.g. sachet, bottle, e.g. containing cefuroxime axetil corresponding to a desired amount of cefuroxime, e.g. in a unit dosage form. A desired amount of cefuroxime axetil includes an amount which correponds to an amount of cefuroxime of 50 to 1000 mg, e.g. 50 to 800 mg, such as 100 to 800 mg, e.g. 100 to 600 mg, e.g. 125 mg, e.g. 250 mg, e.g. 500 mg per unit dosage form.

In another aspect the present invention provides a dosage form comprising a dry powder according to the present invention in a container, e.g. a bottle, sachet, e.g. containing cefuroxime axetil corresponding to a desired amount of cefuroxime, e.g. per dosage form.

Dry powder in a container, e.g. containing cefuroxime axetil corresponding to a desired amount of cefuroxime may e.g. be administered in the form of a suspension/syrup. Dry powder in sachets, e.g. containing cefuroxime axetil according to the present invention corresponding to a desired amount of cefuroxime, e.g. 50 to 1000 mg, e.g. 50 to 800 mg, such as 100 to 800 mg, e.g. 100 to 600 mg, e.g. 125 mg, e.g. 250 mg, e.g. 500 mg, e.g. in a unit dosage form, may e.g. be administered as such, e.g. together with an aqueous liquid, e.g. water, or as a suspension in aqueous liquid, e.g. water, e.g. a sachet may contain a unit dosage form, e.g. and an indication how much aqueous liquid should be used for reconstitution, e.g. to obtain a suspension/syrup. The dry powder may be in a bottle, e.g. having a mark, which indicates the necessary amount of aqueous liquid, e.g. water, to be filled into the bottle for obtaining a desired amount of cefuroxime in a determined volume; e.g. an amount of cefuroxime axetil corresponding to an amount of cefuroxime of 50 to 1000 mg, e.g. 50 to 800 mg, such as 100 to 800 mg, e.g. 100 to 600 mg, e.g. 125 mg, e.g. 250 mg, e.g. 500 mg per a desired volume, e.g. per 3 to 10 ml, e.g. per 5 ml of aqueous liquid.

In another aspect the present invention provides a pharmaceutical dosage form, e.g. unit dosage form, comprising a dry powder according to the present invention in a sachet, containing cefuroxime axetil corresponding to an amount of cefuroxime of 50 to 1000 mg, e.g. 50 to 800 mg, such as 100 to 800 mg, e.g. 100 to 600 mg, e.g. 125 mg, e.g. 250 mg, e.g. 500 mg.

In another aspect the present invention provides a pharmaceutical dosage form comprising a dry powder according to the present invention in a bottle, said bottle having a mark, indicating the necessary amount of aqueous liquid to be filled into the bottle, to obtain an amount of cefuroxime axetil corresponding to a described amount of cefuroxime, e.g. 50 to 1000 mg, e.g. 50 to 800 mg, such as 100 to 800 mg, e.g. 100 to 600 mg, e.g. 125 mg, e.g. 250 mg, e.g. 500 mg; per a determined suspension/syrup volume, e.g. per 3 to 10 ml, e.g. per 5 ml of suspension/syrup.

A dry powder according to the present invention may effect at least 60% (Q-value) dissolution of the labeled amount of cefuroxime axetil within 15 minutes, e.g. and/or at least 75% (Q-value) dissolution of the labeled amount of cefuroxime axetil within 45 minutes; when a dosage form of cefuroxime axetil is tested as set forth in USP test <711> in a USP-2 apparatus under conditions at least as stringent as the following: 900 ml 0.07 N hydrochloric acid, 37° C. with paddles turning at 55 rpm.

A dry powder according to the present invention may be reconstituted with an aqueous liquid, e.g. water. In another aspect the present invention provides a syrup/suspenion for oral administration comprising a dry powder according to the present invention which is reconstituted with an aqueous liquid.

In a preferred embodiment of the present invention a dry powder according to the present invention containing fructose and glucose or a mixture thereof in such an amount that upon reconstitution of said dry powder with an aqueous liquid, e.g. water, e.g. containing an amount of cefuroxime axetil corresponding to a desired amount of cefuroxime, e.g. 50 to 1000 mg, e.g. 50 to 800 mg, such as 100 to 800 mg, e.g. 100 to 600 mg, e.g. 125 mg, e.g. 250 mg, e.g. 500 mg; e.g. per a desired volume, e.g. per 3 to 10 ml, e.g. 5 ml of aqueous liquid, a suspension/syrup is obtained wherein glucose and/or fructose are in highly concentrated, saturated, e.g. supersaturated, solution.

In another aspect the present invention provides cefuroxime axetil, e.g. in a non-gelatinous form on contact with an aqueous liquid, in the form of a dry powder, containing such an amount of fructose and/or glucose that upon reconstitution in an aqueous liquid, e.g. water, of an amount of cefuroxime axetilcorresponding to a desired amount of cefuroxime, e.g. in a desired volume, a suspension/syrup is obtained wherein glucose and/or fructose are in highly concentrated, e.g. saturated or supersatured, solution; e.g. containing in 3 to 10 ml of the highly concentrated solution an amount of cefuroxime axetil, e.g. in non-gelatinous form on contact with an aqueous liquid, e.g. corresponding to 50 to 1000 mg of cefuroxime; and An oral suspension/syrup comprising an effective amount of cefuroxime axetil, e.g. in non-gelatinous form on contact with an aqueous liquid, wherein glucose and/or fructose are in highly concentrated, e.g. saturated or supersaturated, solution.

A granulate of cefuroxime axetil according to the present invention is further useful in the production of tablets, e.g. for the production of tablet cores.

In another aspect the present invention provides a tablet, e.g. a tablet core, e.g. a film coated tablet, e.g. wherein the film coating comprises film-forming polymer, plasticizer, lubricant; e.g. for oral administration, comprising cefuroxime axetilin non-gelatinous form on contact with an aqueous liquid as active ingredient, and pharmaceutically acceptable excipient, e.g. auxiliaries, e.g. which are useful in tablets/tabletting procedure, e.g. disintegrant, and/or binder, and/or lubricant, and/or surface active agent, and/or filler, and/or flow aid; for example binder, and/or surface active agent, and/or filler, and/or flow aid; e.g. wherein said tablet, e.g. film coated, effects at least 60% (Q-value) dissolution of the labeled amount of cefuroxime axetil within 15 minutes, e.g. and/or at least 75% (Q-value) dissolution of the labeled amount of cefuroxime axetil within 45 minutes; when a dosage form of cefuroxime axetil is tested as set forth in USP test <711> in a USP-2 apparatus under conditions at least as stringent as the following: 900 ml 0.07 N hydrochloric acid, 37° C. with paddles turning at 55 rpm.

A tablet, e.g. tablet core, according to the present invention may be e.g. obtained according to a method as conventional, or e.g. as follows: A granulate according to the present invention may be mixed with one or more pharmaceutically acceptable excipients, e.g. auxiliaries which are useful in tablets/tabletting procedure; and the granulate or the mixture with pharmaceutically acceptable excipients may be compressed into tablets, e.g. tablet cores, e.g. by a method as conventional, e.g. optionally comprising compactation steps before compressing. Pharmaceutically acceptable excipients in tablets/tabletting procedure which are preferred in in tablets/tabletting procedure according to the present invention include e.g.

- disintegrants, e.g. which accelerate the release of the active compound, such as starches, e.g. including modified starches, e.g. crosslinked, such as sodium-starch glycolates, croscarmellose sodium, polyvinyl pyrrolidones, e.g. including modified polyvinyl pyrrolidones e.g. crosslinked, such as polyplasdone, crospovidone; celluloses, such as sodium and calcium carboxymethyl celluloses, modified celluloses, e.g. crosslinked; such as AcDiSol; formaldehyde-casein compounds, e.g. Esma-Spreng®, defatted soybean extracts; preferably crosslinked Na carboxymethyl cellulose, e.g. AcDiSol, polyvinyl pyrrolidone, e.g. cross-linked, e.g. polyplasdone and crospovidone; formaldehyde-casein compounds, e.g. Esma-Spreng®; for example crosslinked Na carboxymethyl cellulose, formaldehyde-casein compounds, e.g. formaldehyde-casein compounds;
- binders. e.g. including microcrystalline cellulose, e.g. Avicel®;
- fillers, e.g. including crystalline celluloses, sugars, e.g. mannitol, e.g. Pearlitol®;
- lubricant e.g. including talcum, Mg-stearates, e.g. talcum
- flow aid, e.g. including silicium dioxide, such as Aerosil®,
- surface active agent, e.g. as described above in the production of a granulate according to the present invention; including preferably sodium laurylsulphate, e.g. in mixture with ammonium layrylsulphate, e.g. Texapon®;

preferably e.g. disintegrant, and/or binder, and/or lubricant, and/or surface active agent, and/or filler, and/or flow aid; for example binder, and/or surface active agent, and/or filler.

In a preferred method according to the present invention the process for tablet production may contain further processing steps of an intermediate mixture of pharmaceutically acceptable excipients and/or cefuroxime axetil before compressing, e.g. breaking through a sieve, granulating, compacting. E.g. a granulate according to the present invention, e.g. further processed, e.g. through a sieve, milled; may be granulated, e.g. compacted in mixture with one or more pharmaceutically acceptable excipients, e.g. which are useful in tablets/tabletting procedures, the mixture obtained may be broken up, e.g. processed through a sieve, and mixed with one or more pharmaceutically acceptable excipients, e.g. which are useful in tablets/tabletting procedures. The final mixture obtained may be compressed into tablets/tablet cores, e.g. according to a method as conventional.

In another aspect the present invention provides a process for the production of a tablet, e.g. a tablet core, e.g. a film-coated tablet, e.g. wherein the film coat(ing) comprises film-forming polymer, lubricant, plasticizer, dyestuff and/or flavoring agent; comprising an effective amount of cefuroxime axetilin non-gelatinous form on contact with an aqueous liquid as an active ingredient and pharmaceutically acceptable excipient, e.g. one or more, e.g. which is useful in tablets/tabletting procedure, e.g. auxiliaries, comprising compressing a granulate comprising cefuroxime axetilin non-gelatinous form on contact with an aqueous liquid, according to the present invention, in combination with, e.g. one or more, pharmaceutically acceptable excipient, e.g. which is useful in tablet production/tabletting procedure, e.g. auxiliaries, e.g. disintegrant, and/or binder, and/or lubricant, and/or surface active agent, and/or filler, and/or flow aid; for example one or more binder, and/or surface active agent, and/or filler; e.g and film coating, e.g. according to a method as conventional, e.g. including further processing steps of an intermediate mixture of pharmaceutically acceptable excipients and/or cefuroxime axetil before compressing, e.g. compacting, breaking through a sieve, granulating.

A tablet/tablet core according to the present invention may be coated with a film coat(ing), e.g. according to a method as conventional, e.g. by coating with one or more film-forming components, e.g. with a film-forming composition, e.g. dissolved or suspended in a solvent, e.g. water, an organic solvent or a mixture of water and organic solvent, preferably water, e.g. according to a method as conventional. Preferred film-coating compositions according to the present invention include e.g.

- film-forming polymer; e.g. appropriate celluloses, e.g. hydroxyalkyllceluloses, such as hydroxymethylpropylcellulose, methylcelluloses, e.g. Methocel®, polyvinylpyrrolidones, e.g. Kollidons®, such as Kollidon® VA64; polymethacrylates, e.g. Eudragit®; polyvinyl alcohols;
- plasticizer, e.g polyethyleneglycols;
- lubricant, e.g. talcum;
- dyestuff, pigment, e.g. TiO$_2$, flavoring agent, preservative;

preferably film forming polymer, and/or plasticizer, and/or lubricant, and/or dyestuff, pigment, and/or flavoring agent. A film coat(ing) according to the present invention includes a film coat(ing) having a short rupture time, e.g. as described in EP 223365, i.e. a film coat(ing) which may serve to mask the bitter taste of cefuroxime axetil upon oral administration, the film coat(ing) having a thickness whereby the rupture time is less than 40 seconds when measured by a rupture test, wherein the tablet is placed in a beaker of still 0.07 N hydrochloric acid at 37°, the rupture being measured as the time which elapses before the core of the tablet becomes visible to the naked eye through the ruptured film coat, and the tablet core disintigrating immediately following the rupture of the film coat in said rupture test. The content of EP 223365 referring to film coat(ing) e.g. including the examples for a film coat(ing) as claimed in EP 223365 and the production of tablets coated with a film as claimed in EP 223365, is introduced herein by reference. Preferably according to the present invention a conventional film-coat (ing) having a rupture time of 40 seconds and more is used.

Since cefuroxime axetil, e.g. as commercially available may undergo gelatination, e.g. with the consequence that adsorption of cefuroxime axetil from the gastrointestinal tract may be reduced, e.g. as described herein, up to the present invention a cefuroxime axetil containing tablet usually had an unconventional film-coat(ing) having a very short rupture time, e.g. according to EP 223365, having a rupture time which is less than 40 seconds under defined conditions. A rapidly disintegrating film coat(ing) having a rupture time of less than 40 seconds may e.g. have the disadvantage that the film coat(ing) may be easily destroyed on contact with moisture and the film-coat(ing) looses its protecting effect. It was now surprisingly found, that a tablet comprising cefuroxime axetil in non-gelatinous form on contact with an aqueous liquid may have a conventional coat(ing) having a rupture time which is 40 seconds and more when measured by the rupture test as defined in EP 223365, and keeping, despite of the conventional coat(ing), a dissolution rate in accordance with USP 23 (e.g. USP 24). A tablet comprising cefuroxime axetil having a film coat (ing) the rupture time thereof being 40 seconds and more, e.g. 40 seconds to 10 minutes, e.g. 40 seconds to 3 minutes, when determined in a rupture test according to EP 223365 and having a dissolution rate in accordance with USP 23 (e.g. USP 24) is new.

In another aspect the present invention provides a film coated tablet comprising an effective amount of cefuroxime axetil as an active ingredient and a film coat(ing), the rupture time of the film coat(ing) being 40 seconds and more, e.g. 40 seconds to 10 minutes, when measured by a rupture test, wherein the tablet is placed in a beaker of still 0.07 N hydrochloric acid at 37°, the rupture being measured as the time which elapses before the core of the tablet becomes visible to the naked eye through the ruptured film coat; wherein said film coated tablet effects at least 60% (Q-value) dissolution of the labeled amount of cefuroxime axetil within 15 minutes, e.g. and/or at least 75% (Q-value) dissolution of the labeled amount of cefuroxime axetil within 45 minutes; when a film-coated tablet of cefuroxime axetil is tested as set forth in USP test <711> in a USP-2 apparatus under conditions at least as stringent as the following: 900 ml 0.07 N hydrochloric acid, 37° C. with paddles turning at 55 rpm, e.g. including more stringent conditions, e.g. lower volume of 0.07 N hydrochloric acid, lower temperature, lower paddle speed.

In another aspect the present invention provides the use of a film coat(ing) in the manufacture of a film-coated tablet comprising an effective amount of cefuroxime axetil as an active ingredient and effecting at least 60% (Q-value) dissolution of the labeled amount of cefuroxime axctil within 15 minutes, e.g. and/or at least 75% (Q-value) dissolution of the labeled amount of cefuroxime axetil within 45 minutes under conditions at least as stringent as the following: 900 ml 0.07 N hydrochloric acid, 37° C. with paddles turning at 55 rpm., e.g. including more stringent conditions, e.g. lower volume of 0.07 N hydrochloric acid, lower temperature, lower paddle speed; when a film-coated tablet of cefuroxime axetilis tested as set forth in USP test <711> in a USP-2 apparatus comprising the rupture time of the film coat(ing) being 40 seconds and more, e.g. 40 seconds to 10 minutes, when measured by a rupture test, wherein the film-coated tablet is placed in a beaker of still 0.07 N hydrochloric acid at 37°, the rupture being measured as the time which elapses before the core of the tablet becomes visible to the naked eye through the ruptured film coat(ing).

A tablet having a conventional film-coat(ing) is usually protected against moisture by the film coat(ing). Thus, a film-coated tablet according to the present invention having a rupture time of 40 seconds and more in a rupture test as described above needs not to be sealed against moisture attack in a packaging for a pharmaceutical composition whereas a tablet, having a rupture time of less than 40 seconds may be easily destroyed on contact with moisture and has to be sealed against moisture in a packaging. A packaging for a pharmaceutical composition comprising cefuroxime axetil in a package which lacks sealing against moisture attack is new.

In another aspect the present invention provides a packaging for a pharmaceutical composition, e.g. a container, such as a bottle, comprising cefuroxime axetil as an active ingredient in the form of film-coated tablets comprising an effective amout of cefuroxime axetil, which comprises the packaging lacks sealing against moisture attack and the film-coated-tablets lack sealing against moisture attack.

A film-coated tablet according to the present invention may comprise cefuroxime axetil in an amount corresponding to 50 to 1000 mg cefuroxime as an active ingredient, preferably corresponding to 500 mg, 250 mg or 125 mg cefuroxime.

It is known that commercially available cefuroxime axetil in the form of a tablet and in the form of a dry powder, both comprising the same amount of cefuroxime axetil do not have substantially the same dissolution rates according to USP, i.e. a film coated tablet and a dry powder are not directly interchangable despite containing the same amount of cefuroxime axetil, e.g. a tablet comprising e.g. cefuroxime axetil in an amount corresponding to e.g. 125 mg of cefuroxime cannot be directly replaced by a dry powder comprising cefuroxime axetil in an amount corresponding to 125 mg of cefuroxime because of different dissolution rates, i.e. different bioavailability. It is also known that a dry powder comprising cefuroxime axetil does not fulfil the dissolution requirements of USP 23 but has a dissolution rate of the active ingredient which is different from requirements of USP 23.

It was now surprisingly found that a film-coated tablet and a dry powder, both comprising the same amount of cefuroxime axetil in non-gelatinous form on contact with an aqueous liquid according to the present invention, both have substantially the same dissolution rate according to USP and are thus directly interchangable.

In another aspect the present invention provides the use of cefuroxime axetilin the manufacture of a film-coated tablet which has a dissolution rate according to USP 23 and in the production of a dry powder which has a dissolution rate according to USP 23 wherein the film-coated tablet contains the same effective amount of cefuroxime axetil as the dry powder, e.g. the dry powder and the film-coated tablet are bioequivalent oral administration forms of cefuroxime.

It is known that the absorption and bioavailability of any particular active therapeutic agent, e.g. a drug, may be affected by numerous factors when dosed orally. Such factors include the presence of food in the gastrointestinal tract/stomach. If the bioavailability of a drug is affected beyond a certain point due to the presence of food in the gastrointestinal tract/stomach the drug is said to exhibit a "food effect". It is long known that cefuroxime axetil in the oral forms which are commercially available, e.g. in amorphous form in tablets and in oral dry powders, and crystalline cefuroxime axetil exhibit a food effect, e.g. cefuroxime axetil has a better bioavailability on oral administration in a mammal after consumption of food than in a mammal in the fastened state. Consequently, administration of commercially available cefuroxime axetil is recommended after consumption of food. That food effect of cefuroxime axetil is described to be possibly due to the different pH-conditions in the stomach in fastened state (around pH 1 and below) and in the presence of food (around pH 4). It was now found that the dissolution rate of cefuroxime axetil from pharmaceutical compositions available on the market wherein cefuroxime axetil is in amorphous form is pH dependent; e.g. the release of cefuroxime axetil from the formulation at 37° C. is considerably decreased at a pH of 1 in comparison with the dissolution at pH 4, whereas surprisingly the release of the active compound cefuroxime axetil in a pharmaceutical composition according to the present invention is practically pH-independent, e.g. as shown in FIGS. 1 to 3.

BRIEF DESCRIPTION ON DRAWING

Figure 2:
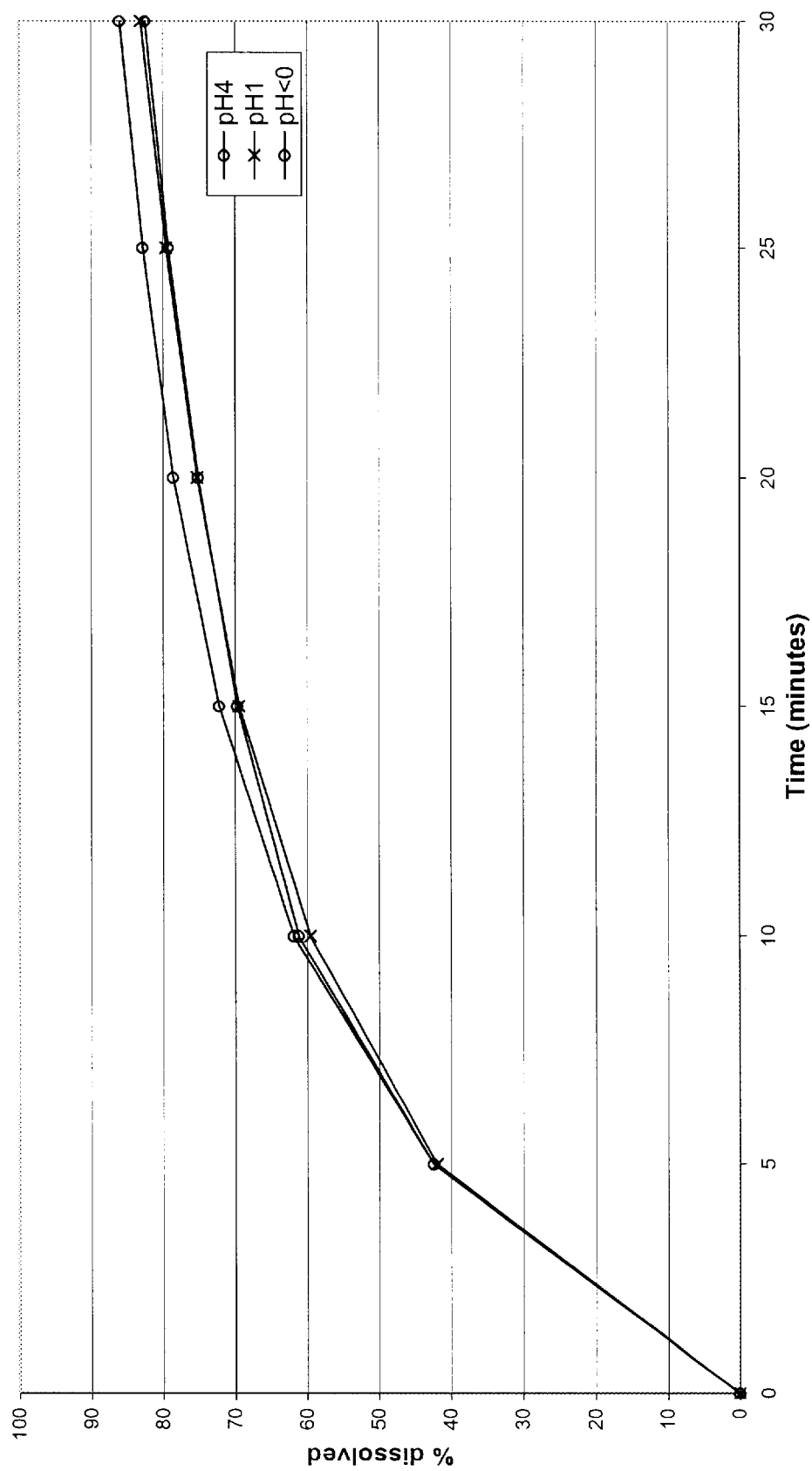

FIGS. 1–3 show the pH dependency of the dissolution rate of cefuroxime axetil.

FIG. 1 shows the pH dependency of the dissolution rate of cefuroxime axetil in a 500 mg film-coated tablet available on the market under the trade name Zinnat® at pH 1, pH<0 and pH 4 at 37° C. in % dissolution of labeled amount of cefuroxime axetil in a defined time period (in minutes). From FIG. 1 it is e.g. evident that the dissolution rate of cefuroxime axetil in a film coated tablet commercially available on the market at 37° C. in aqueous medium, e.g. acidic, e.g. hydrochloric acid-acidic, e.g. buffered, is lower
than 5% at a pH of around 1, e.g. at pH 1 after 10 to 15 minutes from the start of the dissolution test; and/or
than 20% at a pH<0 after 25 to 30 minutes from the start of the dissolution test,
than the dissolution rate of cefuroxime axetil at a pH of around 4, e.g. at pH 4.

FIG. 2 shows the pH dependency of the dissolution rate of cefuroxime axetil in a 500 mg film-coated tablet according to the present invention, i.e. comprising cefuroxime axetil in non-gelatinous form on contact with an aquous liquid, e.g. prepared according to example 13 of the present application, at pH 1, pH<0 and pH 4 at 37° C. in % dissolution of labeled amount of cefuroxime axetil in a defined time period (in minutes). From FIG. 2 it is e.g. evident that the dissolution rate of cefuroxime axetil in a film coated according to the present invention at 37° C. in aqueous medium, e.g. acidic, e.g. hydrochloric acid-acidic, e.g. buffered, is equal or not lower
than 5% at a pH of around 1, e.g. at pH 1 after 10 to 15 minutes from the start of the dissolution test; and/or
than 20% at a pH<0 after 25 to 30 minutes from the start of the dissolution test,
than the dissolution rate of cefuroxime axetil at a pH of around 4, e.g. at pH 4.

FIG. 3 shows the pH dependency of the dissolution rate of cefuroxime axetil
of a 500 mg film-coated tablet according to the present invention i.e. comprising cefuroxime axetil in non-gelatinous form on contact with an aquous liquid, prepared according to example 13 of the present application (Invention); and
of a 500 mg film-coated tablet prepared according to example 19 of the present application, comprising amorphous cefuroxime axetil, e.g. as commercially available, instead of cefuroxime axetil in non-gelatinous form by replacing the granulation Step A by a conventional mixing step (Prior Art).

at pH<0 at 37° C. in % dissolution of labeled amount of cefuroxime axetil in a defined time period (in minutes). From FIG. 3 it is e.g. evident that the dissolution rate of amorphous cefuroxime axetil is different than the dissolution rate of cefuroxime axetil in non-gelatinous form on contact with an aqueous liquid.

The dissolution rate of cefuroxime axetil as shown in to FIGS. 1 to 3 may preferably be determined as set forth in USP test <711> which is described in more detail above.

Since usually the pH is increased in the stomach in the presence of food to around pH 4 compared with a pH of around 1 and below in the fastened state, the food effect of cefuroxime axetil is believed to be due to the pH dependent dissolution rate of amorphous cefuroxime axetil in a form as commercially available. It was on the other hand surprisingly found that the dissolution rate of cefuroxime axetil in non-gelatinous form according to the present invention, e.g. in the form of a tablet or a granulate is practically pH independent. Consequently, a tablet or a granulate comprising cefuroxime axetil in non-gelatinous form according to the present invention may be administered independently whether a mammal has eaten or is in the fastend state, e.g. cefuroxime axetil according to the present invention does not exhibit an adverse food effect.

The use of cefuroxime axetil in the manufature of an oral dosage form which does not exhibit an adverse food effect is new.

In another aspect the present invention provides the use of cefuroxime axetil in the manufacture of an oral dosage form, e.g. a tablet or a dry powder or a suspension/syrup for oral administration, which does not exhibit an adverse food effect in the treatment of microbial, e.g. bacterial, infection in a mammal, e.g. and wherein said dosage form effects at least 60% (Q-value) dissolution of the labeled amount of cefuroxime axetil within 15 minutes, e.g. and/or at least 75% (Q-value) dissolution of the labeled amount of cefuroxime axetil within 45 minutes; when a dosage form of cefuroxime axetilis tested as set forth in USP test <711> in a USP-2 apparatus under conditions at least as stringent as the following: 900 ml 0.07 N hydrochloric acid, 37° C. with paddles turning at 55 rpm; e.g. including more stringent conditions, e.g. lower volume of 0.07 N hydrochloric acid, lower temperature, lower paddle speed, e.g. wherein said mammal is a human.

In another aspect the present invention provides an oral dosage form of cefuroxime axetil which is in the form of a tablet, e.g. film-coated, e.g. conventionally film-coated, which is administrable to a mammal that is in the fastened state and which exhibits no adverse food effect, which comprises an effective amount of cefuroxime axetil and pharmaceutically acceptable excipients, e.g. disintegrant, and/or binder, and/or filler, and/or lubricant, and/or flow aid and/or surface active agent, said dosage form effects at least 60% (Q-value) dissolution of the labeled amount of cefuroxime axetil within 15 minutes, e.g. and/or at least 75% (Q-value) dissolution of the labeled amount of cefuroxime axetil within 45 minutes; when a dosage form of cefuroxime axetilis tested as set forth in USP test <711> in a USP-2 apparatus under conditions at least as stringent as the following: 900 ml 0.07 N hydrochloric acid, 37° C. with paddles turning at 55 rpm; e.g. including more stringent conditions, e.g. lower volume of 0.07 N hydrochloric acid, lower temperature, lower paddle speed; e.g. wherein said mammal is a human.

In another aspect the present invention provides an oral dosage form containing cefuroxime axetil as an active ingredient which is in the form of a dry powder or which is in the form of a suspension/syrup and which is administrable to a mammal that is in the fastened state and which exhibits no adverse food effect, which comprises an effective amount of cefuroxime axetil and one or more pharmaceutically acceptable excipient, sugar and/or sweetener and/or filler and/or thickener, and/or preservative, e.g. said dry powder effects at least 60% (Q-value) dissolution of the labeled amount of cefuroxime axetil within 15 minutes, e.g. and/or at least 75% (Q-value) dissolution of the labeled amount of cefuroxime axetil within 45 minutes; when a dosage form of cefuroxime axetilis tested as set forth in USP test <711> in a USP-2 apparatus under conditions at least as stringent as the following: 900 ml 0.07 N hydrochloric acid, 37° C. with paddles turning at 55 rpm, e.g. including more stringent conditions, e.g. lower volume of 0.07 N hydrochloric acid, lower temperature, lower paddle speed; e.g. wherein said mammal is a human.

In another aspect the present invention provides processes for the production of granulates comprising cefuroxime axetil, in which the active ingredient cefuroxime axetil is present in an activated form so that it no longer has a tendency to form a gel when in contact with aqueous media, characterised in that granulation is carried out under addition of a polymer or an insoluble adsorbent.

The following examples illustrate the present invention.

EXAMPLES 1 TO 13

Step A. Preparation of a Granulate Comprising Cefuroxime Axetil in Non-gelatinous Form on Contact with an Aqueous Liquid and Other Components as Indicated in TABLE 1 and TABLE 2

The amount of cefuroxime axetil in TABLE 1 and TABLE 2 (in mg/per tablet) is indicated in the corresponding amount of cefuroxime which is the active amount in vivo because in vivo the carboxylic ester in position 4 of the ring system is split off, the carboxylic acid is set free and the compound cefuroxime is formed.

General Procedure in Examples 1 to 5 and 10 to 12

A fluid of solid component VI and VII as set out in TABLES 1 and 2 (if present in the corresponding example according to TABLE 1 and TABLE 2) in a fluidized bed granulator is treated (sprayed) with a solution/suspension of components I to IV as set out in TABLE 1 and TABLE 2 (if present in the corresponding example according to TABLE 1 and TABLE 2). As a solvent acetone is used in examples 1 to 5 and a mixture of acetone:water (ca. 7:1) in examples 10 to 12. The dry granulate obtained is processed through a sieve (e.g. 210 $\mu$m, 250 $\mu$m, 500 $\mu$m, 630 $\mu$m) or milled.

General Procedure in Examples 6 and 13 to 15

A solution of components I, II, and III as set out in TABLE 1 and TABLE 2 (if present in the corresponding example according to TABLE 1 and TABLE 2) is granulated in a spray dryer. As a solvent acetone is used in example 6 and a mixture of acetone:water (ca. 7:1) in examples 13 to 15. A dry granulate is obtained.

General Procedure in Example 7

Component IV as set out in TABLE 2 is moistened with a solution of components I, II and III as set out in TABLE 2 in acetone in portions and the mixture obtained is granulated under mixing and the mixture otained is dried. The dry granulate obtained is processed through a sieve (500 $\mu$m) and milled after sieve processing.

General Procedure in Examples 8 and 9

From a solution/suspension of components I, IV and V as set out in TABLE 2 (if present in the corresponding example according to TABLE 2) the solvent is evaporated off in a rotovapor. In example 8 ethanol and in example 9 methylene chloride is used as a solvent. The dry granulate obtained is processed through a sieve and milled after sieve processing.

TABLE 1

| | | Example No./amount in examples given in mg/tablet | | | | | | | |
|---|---|---|---|---|---|---|---|---|---|
| No. | Component | 1 | 2. | 3 | 4 | 5 | 6 | 7 | 8 |
| I | Cefuroxime axetil corresponding to cefuroxime | 250 | 125 | 500 | 500 | 250 | 250 | 250 | 250 |
| II | Kollidon ® VA 64 | 122.5 | — | 70 | — | 121.5 | 76 | 121.5 | — |
| III | Sodium lauryl sulphate | 3 | 1.5 | 6 | 6 | 3 | 2.5 | 3 | — |
| IV | Aerosil ® | — | 60 | — | 66 | — | — | 250 | 100 |
| V | Kollidon ® | — | — | — | — | — | — | — | 100 |
| VI | Mannitol, e.g. Pearlitol ® | 150 | 76 | 86 | 90 | 100 | — | — | — |
| VII | Talcum | — | — | — | — | 1.5 | — | — | — |

TABLE 2

| | | Example No./amount in examples given in mg/tablet | | | | | | |
|---|---|---|---|---|---|---|---|---|
| No. | Component | 9 | 10 | 11 | 12 | 13 | 14 | 15 |
| I | Cefuroxime axetil corresponding to cefuroxime | 125 | 500 | 500 | 500 | 500 | 250 | 125 |
| II | Kollidon ® VA 64 | — | 243 | 243 | 243 | 243 | 121.5 | 60.8 |
| III | Sodium lauryl sulphate | — | 6 | 6 | 6 | 6 | 3 | 1.5 |
| IV | Aerosil ® | — | — | — | — | — | — | — |
| V | Kollidon ® 25 | 150 | — | — | — | — | — | — |
| VI | Mannitol, e.g. Pearlitol ® | — | 200 | 200 | 200 | — | — | — |
| VII | Talcum | — | 2 | — | — | — | — | — |

B. Production of a Mixture for Tabletting Comprising a Granulate which Comprises Cefuroxime Axetil in Non-gelatinous Form on Contact with an Aqueous Liquid and Other Components as Indicated in TABLE 4 and TABLE 5

TABLE 4

| No. | Component | \multicolumn{8}{c}{Example No./amount in examples given in mg/tablet} | | | | | | | |
|---|---|---|---|---|---|---|---|---|---|
| | | 1 | 2. | 3 | 4 | 5 | 6 | 7 | 8 |
| VIII | Ac-Di-Sol | 37.5 | 20 | — | 140 | 30 | 20 | 40 | — |
| IX | Crospovidone, Polyplasdone | 37.5 | 20 | 125 | — | 30 | 20 | 40 | 65 |
| X | Talcum | 12.5 | 6 | 10 | 8 | 10 | 10 | 10 | 8 |
| XI | Aerosil ® | 21 | 11 | 16 | 11 | 15 | 15 | 15 | 9.5 |
| XII | Sodium laurylsulphate | 7 | 4 | 9 | 8 | 5 | 7 | 7 | 8.5 |
| XIII | Mg-stearate | 5 | 2.5 | 8 | 8 | 4.5 | 4.5 | 5 | 5 |
| XIV | Ca-carboxymethylcellulose | — | — | 25 | — | — | — | — | — |
| XV | Microcrystalline cellulose | — | — | 30 | 48 | 60 | 30 | 60 | 24 |
| XVI | Esma-Spreng ® | — | — | — | — | — | — | — | — |
| XVII | Mannitol, e.g. Pearlitol ® | — | — | — | — | — | — | — | — |

TABLE 5

| No. | Component | \multicolumn{7}{c}{Example No./amount in examples given in mg/tablet} | | | | | | |
|---|---|---|---|---|---|---|---|---|
| | | 9 | 10 | 11 | 12 | 13 | 14 | 15 |
| VIII | Ac-Di-Sol | 25 | — | 80 | 80 | 150 | 76 | 38 |
| IX | Crospovidone, Polyplasdone | 13 | 80 | 80 | 80 | 40 | 20 | 10 |
| X | Talcum | 6 | 40 | 30 | 30 | 14 | 7 | 3.5 |
| XI | Aerosil ® | 10 | 40 | 33 | 33 | 36 | 18 | 9 |
| XII | Sodium laurylsulphate | 3.5 | 14 | 14 | 14 | 12 | 6 | 1.5 |
| XIII | Mg-stearate | 2.5 | 20 | 15 | 15 | 8 | 4 | 2 |
| XIV | Ca-carboxymethylcellulose | — | — | — | — | — | — | — |
| XV | Microcrystalline cellulose | — | 121 | — | — | 30 | 15 | 7.5 |
| XVI | Esma-Spreng ® | — | 80 | 80 | 80 | — | — | — |
| XVII | Mannitol, e.g., Pearlitol ® | — | — | — | — | 90 | 45 | 22.5 |

General Procedure in Examples 1 to 4, 7 to 9

The granulate obtained in Step A is mixed with components VIII to XIII as set out in TABLE 4 and TABLE 5 (if present in the corresponding example according to TABLE 4 and TABLE 5) and the mixture obtained is compressed into tablets.

General Procedure in Example 5 and Example 6

The granulate obtained in step A is mixed with component XV and compressed, the comprimate obtained is processed through a sieve and mixed with components VIII, IX, X, XI, XII and XIII. The mixture obtained is compressed into tablets. Components VIII, IX, X, XI, XII, XIII and XV are as set out in TABLE 4 (if present in the corresponding example according to TABLE 4).

General Procedure in Example 10

The granulate obtained in step A is mixed with components XV and 30 mg/tablet of component XI. The mixture obtained is compacted and the comprimate obtained is processed through a 1.00 mm sieve and the granules obtained are mixed with component X, 10 mg/tablet of component XI and components XIII, XII, IX and XVI. The mixture obtained is compressed into tablets. Components IX, XI, XII, XIII, XV and XVI are as set out in TABLE 5.

General Procedure in Examples 11 and 12

The granulate obtained in step A is mixed with component XVI and 30 mg/tablet of component XI. The mixture obtained is compacted and the comprimate obtained is processed through a 630 μm sieve and the granules obtained are mixed with component VIII, 3 mg/tablet of component XI and components X, XIII, XII, IX and XVI. The mixture obtained is compressed into tablets. Components VIII, IX, X, XI, XII, XIII, and XVI are as set out in TABLE 5.

General Procedure in Examples 13

The granulate obtained in step A is mixed with 110 mg/tablet of component VIII, 30 mg/tablet of component XI and 5 mg/tablet of component XIII. The mixture obtained is compacted and the comprimate obtained is processed through a 630 μm sieve and the granules obtained are mixed with 40 mg/tablet of component VIII, 6 mg/tablet of component XI, 3 mg/tablet of component XIII and with components X, XII, IX, XV and XVII. The mixture obtained is compressed into tablets, Components VIII, IX, X, XI XII, XIII XV and XVII are as set out in TABLE 5.

General Procedure in Examples 14 and 15

55 mg/tablet (27.5 mg/tablet) of component VIII, 15 mg/tablet (7.5 mg/tablet) of component XI and 2.5 mg/tablet (1.2 mg/tablet) of component XIII are mixed with the granulate obtained in step A. The mixture obtained is compacted and the comprimate obtained is processed through a 630 μm sieve. The granules obtained are mixed with 21 mg/tablet (10.5 mg/tablet) of component VIII, 3 mg/tablet (1.5 mg/tablet) of component XI, and 1.5 mg of component XIII and with components IX, X, XI, XII, XV and XVII. The mixture obtained is compressed into tablets. Components VIII, IX, X, XI XII, XIII XV and XVII are as set out in TABLE 5.

C. Production of Film-coated Tablets from Tablets Produced in Step B Comprising Coating Components as Indicated in TABLE 6 and TABLE 7

TABLE 6

| No. | Component | 1 | 2. | 3 | 4 | 5 | 6 | 7 | 8 |
|---|---|---|---|---|---|---|---|---|---|
| XVIII | Hydroxypropyl-methylcellulose, e.g. Methocel ® | 65 | 65 | 59.6 | 59.6 | 65 | 65 | 65 | 65 |
| XIX | Polyethylen-glycol ® 6000 | 10 | 10 | 9.2 | 9.2 | 10 | 10 | 10 | 10 |
| XX | TiO$_2$ | 20 | 20 | 18.3 | 18.3 | 20 | 20 | 20 | 20 |
| XXI | Talcum | 5 | 5 | 4.6 | 4.6 | 5 | 5 | 5 | 5 |
| XXII | Kollidon ® VA64 | — | — | 8.3 | 8.3 | — | — | — | — |

Example No./amount in examples given in weight %

TABLE 7

| No. | Component | 9 | 10 | 11 | 12 | 13 | 14 | 15 |
|---|---|---|---|---|---|---|---|---|
| XVIII | Hydroxypropylmethyl-cellulose, e.g. Methocel ® | 59.1 | 36.8 | 53.6 | 53.6 | 53.6 | 52.2 | 54.5 |
| XIX | Polyethylenglycol ® 6000 | 9.1 | — | — | — | — | 4.3 | — |
| XX | TiO$_2$ | 18.2 | 31.6 | 19.6 | 19.6 | 19.6 | 17.4 | 18.2 |
| XXI | Talcum | 4.5 | 31.6 | 26.8 | 26.8 | 26.8 | 26.1 | 27.3 |
| XXII | Kollidon ® VA64 | 9.1 | — | — | — | — | — | — |

Example No./amount in examples given in weight %

General Procedure in Examples 1 to 15

Components XVIII to XXII as set out in TABLE 6 and TABLE 7 (if present according to TABLE 6 and TABLE 7 in the corresponding example) are dissolved or suspended, respectively in water and tablets obtained in Step B are film-coated with the suspension obtained. The film-coated tablets are dried. The thickness of a coating is such, that the rupture time of the film coated tablets, e.g. determined as described in EP 233365 and as described herein above is in average from 1 to 2, e.g. around 1.5 minutes. Dissolution of the active component from tablets obtained according to examples 1 to 15 complies with the requirements of USP 23 (and USP 24 which is provided and supposed to be in force from the year 2000).

EXAMPLES 16 TO 19

Production of Oral Dry Powder Comprising Cefuroxime Axetil in Non-gelatinous Form on Contact with an Aqueous Liquid, Suitable for the Production of a Suspension/syrup General Procedure A granulate obtained according to example 1, Step A or according to example 2, Step A or according to Example 13, Step A, either as such, or after compactation and processing through a 630 μm sieve, is mixed with components XXIII to XXX as set out in TABLE 8 (if present according to TABLE 8 in the corresponding example) to homogeneity. A mixture in the form of a dry powder is obtained which may be used in oral administration of cefuroxime axetil. The homogenous mixture obtained is either treated with water to form an oral suspension/syrup in such an amount that 5 ml of a reconstituted suspension contain an amount of cefuroxime axetil which corresponds to 125, 250 or 500 mg of cefuroxime;
   filled into a bottle, e.g. which carry a mark indicating the necessary amount of aqueous liquid to obtain 125, 250 or 500 mg of cefuroximein 5 ml of oral suspension/syrup; or filled into sachets in such an amount that one sachet contains an amount of cefuroxime axetil which corresponds to 125, 250 or 500 mg of cefuroxime.

TABLE 8

| No. | Component | 17 289.8[1] | 16 18 579.62[2] | 1208.1[3] |
|---|---|---|---|---|
| | Granulate obtained according to Step A of examples 1, 2 or 13 | | | |
| XXIII | Glucose | 700 | 1500 | 500 |
| XXIV | Fructose | 1200 | 1500 | 3500 |
| XXV | Aspartame | 15 | 15 | 10 |
| XXVI | Strawberry flavoring | 40 | 40 | 40 |

Example No./amount in examples given in mg/tablet

TABLE 8-continued

| No. | Component | 17 289.8[1] | 16 18 579.62[2] | 1208.1[3] |
|---|---|---|---|---|
| | Granulate obtained according to Step A of examples 1, 2 or 13 | | | |
| XXVII | Caramel flavoring | 40 | 40 | 50 |
| XXVIII | Saccharose | 2000 | 1000 | 2200 |
| XXIX | Guar flour | 15 | 15 | — |
| XXX | Starch ®1500 | 400 | 400 | — |

Example No./amount in examples given in mg/tablet

[1]: corresponding to 125 mg cefuroxime
[2]: corresponding to 250 mg cefuroxime
[3]: corresponding to 500 mg cefuroxime

EXAMPLE 19

Comparison

The components are as for example 13, Step A, Step B and Step C in the same amounts as listed in TABLE 2, TABLE 4 and TABLE 6. Cefuroxime axetil (amorph), Kollidon VA64, mannitol, Esma-Spreng® and 6 mg sodium laurylsulphate are mixed. The mixture is compacted and the comprimate obtained is processed through a 1.00 mm sieve. The granulate obtained is mixed with Polyplasdone, Ac-Di-Sol, microcrystalline cellulose, talcum, Mg-stearate and the rest of sodiumlauryl sulphate and compressed. The tablets are film-coated as described in Example 13 C. The dissolution rate of film-coated tablets obtained is shown in FIG. 3.

What is claimed is:

1. Cefuroxime axetil in a non-gelatinous form on contact with an aqueous liquid comprising cefuroxime axetil in the form of a solid solution dissolved in a polymer.

2. Cefuroxime axetil according to claim 1, wherein the weight ratio of cefuroxime axetil:polymer is 1:0.15 to 1:06.

3. A pharmaceutical compositions comprising a pharmaceutically effective amount of cefuroxime axetil in non-gelatinous form on contact with an aqueous liquid according to claim 1 as an active ingredient in combination with pharmaceutically acceptable excipient.

4. A pharmaceutical composition according to claim 1, in the form of a pharmaceutical dosage form wherein said dosage form effects at least 60% (Q-value) dissolution of the labeled amount of cefuroxime axetil within 15 minutes and/or at least 75% (Q-value) dissolution of the labeled amount of cefuroxime axetil within 45 minutes; when said dosage form of cefuroxime axetilis tested as set forth in USP test <711> in a USP-2 apparatus under conditions at least as stringent as the following: 900 ml 0.07 N hydrochloric acid, 37° C. with paddles turning at 55 rpm.

5. A dry powder for oral administration comprising an effective amount of cefuroxime axetil in non-gelatinous form on contact with an aqueous liquid according to claim 1 as an active ingredient and pharmaceutically acceptable excipient.

6. A dry powder according to claim 5 in a container, containing cefuroxime axetil in an amount corresponding to an effective amount of cefuroxime.

7. A syrup/suspenion for oral administration comprising a dry powder according to claim 5 which is reconstituted with an aqueous liquid.

8. A suspension/syrup according to claim 7 for oral administration comprising an effective amount of cefuroxime axetil wherein glucose and/or fructose are in highly concentrated solution.

9. A tablet for oral administration comprising an effective amount of cefuroxime axetil in non-gelatinous form on contact with an aqueous liquid as an active ingredient according to claim 1, and pharmaceutically acceptable excipient.

10. A tablet according to claim 9 which is film-coated.

11. A film-coated tablet comprising cefuroxime axetil according to claim 1 as an active ingredient and a film coat(ing), a rupture time of the film coat(ing) being 40 seconds and more when measured by a rupture test, wherein the tablet is placed in a beaker of still 0.07 M hydrochloric acid at 37°, the rupture being measured as the time which elapses before the core of the tablet becomes invisible to the naked eye through the ruptured film coat; wherein said film coated tablet effects at least 60% (Q-value) dissolution of the labeled amount of cefuroxime axetil within 15 minutes, when the film-coated tablet of cefuroxime axetil is tested as set forth in USP test <711> in a USP-2 apparatus under conditions at least as stringent as the following: 900 mL 0,07 N hydrochloric acid, 37° C. with paddles turning at 55 rpm.

12. A packaging for a pharmaceutical composition comprising cefuroxime axetil according to claim 1 as an active ingredient in the form of film-coated tablets comprising an effective amount of cefuroxime axetil, which comprises the packaging lacks sealing against moisture attack and the film-coated tablets lack sealing against moisture attack.

13. A process for the production of a tablet according to claim 9 comprising an effective amount of cefuroxime axetilin non-gelatinous form on contact with an aqueous liquid as an active ingredient, which comprises compressing a granulate of cefuroxime axetil and a polymer and/or an adsorbent wherein cefuroxime axetil is in non-gelatinous form on contact with an aqueous liquid and one or more pharmaceutically acceptable excipients in mixture with one or more pharmaceutically acceptable excipients and, if desired, film coating.

14. An oral dosage form of cefuroxime axetil according to claim 1 which is in the form of a tablet which is administrable to a mammal that is in the fastened state and which exhibits no adverse food effect, which comprises an effective amount of cefuroxime axetil and pharmaceutically acceptable excipient.

15. An oral dosage form of cefuroxime axetil according to claim 1 which is in the form of a dry powder or which is in the form of a suspension/syrup and which is administrable to a mammal that is in the fastened state and which exhibits no adverse food effect, which comprises an effective amount of cefuroxime axetil and pharmaceutically acceptable excipient.

16. An oral dosage form according to claim 14 which effects at least 60% (Q-value) dissolution of the labeled amount of cefuroxime axetil within 15 minutes and/or at least 75% (Q-value) dissolution of the labeled amount of cefuroxime axetil within 45 minutes; when a dosage form of cefuroxime axetilis tested as set forth in USP test <711> in a USP-2 apparatus under conditions at least as stringent as the following: 900 ml 0.07 N hydrochloric acid, 37° C. with paddles turning at 55 rpm.

17. A process for the production of granulates comprising cefuroxime axetil according to claim 1, in which the active ingredient cefuroxime axetil is present in an activated form so that it no longer has a tendency to form a gel when in contact with aqueous media, characterized in that granulation is carried out under addition of a polymer or an insoluble adsorbent.

18. Cefuroxime axetil in a non-gelatinous form on contact with an aqueous liquid comprising cefuroxime axetil in the form of a solid dispersion on an adsorbent.

19. A pharmaceutical compositions comprising a pharmaceutically effective amount of cefuroxime axetil in non-gelatinous form on contact with an aqueous liquid according to claim 18 as an active ingredient in combination with pharmaceutically acceptable excipient.

20. A pharmaceutical composition according to claim 1, in the form of a pharmaceutical dosage form wherein said dosage form effects at least 60% (Q-value) dissolution of the labeled amount of cefuroxime axetil within 15 minutes when said dosage form of cefuroxime axetil is tested as set forth in USP test <711> in a USP-2 apparatus under conditions at least as stringent as the following: 900 mL, 0,07 N hydrochloride acid, 37° C. with paddles turning at 55 rpm.

21. A dry powder for oral administration comprising an effective amount of cefuroxime axetil in non-gelatinous form on contact with an aqueous liquid according to claim 18 as an active ingredient and pharmaceutically acceptable excipient.

22. A tablet for oral administration comprising an effective amount of cefuroxime axetil in non-gelatinous form on contact with an aqueous liquid as an active ingredient according to claim 18, and pharmaceutically acceptable excipient.

23. A film-coated tablet comprising cefuroxime axetil according to claim 18 as an active ingredient and a film coat(ing), a rupture time of the film coat(ing) being 40 seconds and more when measured by a rupture test, wherein the tablet is placed in a beaker of still 0.07 M hydrochloric acid at 37°, the rupture being measured as the time which elapses before the core of the tablet becomes invisible to the naked eye through the ruptured film coat; wherein said film coated tablet effects at least 60% (Q-value) dissolution of the labeled amount of cefuroxime axetil within 15 minutes, when the film-coated tablet of cefuroxime axetil is tested as set forth in USP test <711> in a USP-2 apparatus under conditions at least as stringent as the following: 900 mL 0,07 N hydrochloric acid, 37° C. with paddles turning at 55 rpm.

24. Cefuroxime axctil in non-gelatinous form on contact with an aqueous liquid which comprises cefuroxime axetil in the form of a solid solution dissolved in a polymer in combination with cefuroxime axetil in the form of a solid dispersion on an adsorbent.

25. A granulate of cefuroxime axetil in a non-gelatinous form on contact with an aqueous liquid comprising cefuroxime axetil dissolved in a polymer and/or an adsorbent; and pharmaceutically acceptable excipient.

26. A process for the production of cefuroxime axetil in non-gelatinous form on contact with an aqueous liquid comprising dissolving or suspending cefuroxime axetil and a polymer in an organic solvent which is able to form a non-gelatinous solid together with cefuroxime axetil and/or a carrier which is able to form a surface solid dispersion with cefuroxime axetil in the organic solvent and removing the solvent.

27. A process for the production of a granulate wherein cefuroxime axetil is in non-gelatinous form on contact with an aqueous liquid, comprising removing solvent from a suspension or solution containing cefuroxime axetil and a polymer which is able to form a non-gelatinous solid on contact with an aqueous liquid; and adding optionally, pharmaceutically acceptable excipients.

28. A process for the production of a granulate wherein cefuroxime axetil is in non-gelatinous form on contact with an aqueous liquid, comprising removing solvent from a suspension or solution containing cefuroxime axetil and an adsorbent which is able to form a surface solid dispersion with cefuroxime axetil; and optionally adding pharmaceutically acceptable excipients.

* * * * *